US009896645B2

(12) United States Patent
Cetti et al.

(10) Patent No.: US 9,896,645 B2
(45) Date of Patent: Feb. 20, 2018

(54) PERSONAL CARE COMPOSITIONS

(71) Applicant: The Procter & Gamble Company, Cincinnati, OH (US)

(72) Inventors: Jonathan Robert Cetti, Mason, OH (US); Steven Edward Witt, Morrow, OH (US); Timothy Alan Scavone, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 105 days.

(21) Appl. No.: 14/209,427

(22) Filed: Mar. 13, 2014

(65) Prior Publication Data

US 2014/0274870 A1    Sep. 18, 2014

Related U.S. Application Data

(60) Provisional application No. 61/790,378, filed on Mar. 15, 2013.

(51) Int. Cl.
*C11B 9/00* (2006.01)
*A61K 31/715* (2006.01)
*A61K 31/724* (2006.01)
*A61Q 13/00* (2006.01)
*A61K 8/73* (2006.01)
*A61K 8/04* (2006.01)
*A61K 8/34* (2006.01)
*A61K 8/362* (2006.01)
*A61Q 15/00* (2006.01)

(52) U.S. Cl.
CPC ............ *C11B 9/0069* (2013.01); *A61K 8/046* (2013.01); *A61K 8/34* (2013.01); *A61K 8/345* (2013.01); *A61K 8/362* (2013.01); *A61K 8/738* (2013.01); *A61K 31/715* (2013.01); *A61K 31/724* (2013.01); *A61Q 13/00* (2013.01); *A61Q 15/00* (2013.01); *A61K 2800/30* (2013.01)

(58) Field of Classification Search
CPC .............................. C11B 9/0069; A61K 8/046
See application file for complete search history.

(56) References Cited

U.S. PATENT DOCUMENTS

| | | |
|---|---|---|
| 4,803,195 A | 2/1989 | Holzner |
| 5,135,747 A | 8/1992 | Faryniarz et al. |
| 5,176,903 A | 1/1993 | Goldberg et al. |
| 5,378,468 A | 1/1995 | Suffis et al. |
| 5,380,707 A | 1/1995 | Barr et al. |
| 5,508,259 A | 4/1996 | Holzner et al. |
| 5,578,563 A | 11/1996 | Trinh et al. |
| 5,580,851 A | 12/1996 | Trinh et al. |
| 5,626,856 A | 5/1997 | Berndt |
| 5,711,941 A | 1/1998 | Behan et al. |
| 5,780,020 A | 7/1998 | Peterson et al. |
| 5,861,144 A | 1/1999 | Peterson et al. |
| 5,874,067 A | 2/1999 | Lucas et al. |
| 5,879,666 A | 3/1999 | Lucas et al. |
| 5,882,638 A | 3/1999 | Dodd et al. |
| 5,897,855 A | 4/1999 | Trinh et al. |
| 5,932,198 A | 8/1999 | Goldman et al. |
| 5,932,199 A | 8/1999 | Esser |
| 6,036,964 A | 3/2000 | Guenin et al. |
| 6,110,449 A | 8/2000 | Bacon et al. |
| 6,123,932 A | 9/2000 | Guskey et al. |
| 6,165,452 A | 12/2000 | Boden et al. |
| 6,180,121 B1 | 1/2001 | Guenin et al. |
| 6,306,818 B1 | 10/2001 | Anderson et al. |
| 6,495,097 B1 | 12/2002 | Streit et al. |
| 6,509,010 B2 | 1/2003 | Beck et al. |
| 6,752,982 B2 | 6/2004 | Colwell et al. |
| 6,793,915 B1 | 9/2004 | Guenin et al. |
| 6,805,855 B2 | 10/2004 | Mattai et al. |
| 6,835,373 B2 | 12/2004 | Kolodzik et al. |
| 6,869,923 B1 | 3/2005 | Cunningham et al. |
| 6,893,647 B1 * | 5/2005 | Malton ................. A61K 8/738 424/401 |
| 6,984,617 B2 | 1/2006 | Holland et al. |
| 7,041,337 B2 | 5/2006 | Heltovics et al. |
| 7,067,152 B2 | 6/2006 | Shefer et al. |
| 7,208,462 B2 * | 4/2007 | Heltovics ................. A61K 8/11 424/76.4 |
| 7,208,463 B2 * | 4/2007 | Heltovics ................. A61K 8/60 424/76.4 |
| 7,208,464 B2 | 4/2007 | Heltovics et al. |
| 7,208,465 B2 | 4/2007 | Heltovics et al. |
| 7,235,261 B2 | 6/2007 | Smith et al. |
| 7,407,650 B2 * | 8/2008 | Heltovics ............... A61Q 13/00 424/76.4 |
| 7,413,731 B2 * | 8/2008 | Heltovics ............... A61Q 13/00 424/76.4 |

(Continued)

FOREIGN PATENT DOCUMENTS

EP    0 535 942 B1    2/1999
EP    0 966 258 B1    5/2003

(Continued)

OTHER PUBLICATIONS

U.S. Appl. No. 14/210,523, filed Mar. 14, 2014, Timothy Alan Scavone et al.

(Continued)

*Primary Examiner* — Lanee Reuther

(74) *Attorney, Agent, or Firm* — Kathleen Y. Carter; Carrie M. Schwartz

(57) ABSTRACT

Aerosolized compositions including a cyclic oligosaccharide; a fragrance; a volatile solvent; and a propellant; wherein the aerosolized composition is free of nonvolatile solvents are described herein. The aerosolized compositions and methods disclosed herein may provide a longer lasting fragrance.

7 Claims, No Drawings

(56) References Cited

U.S. PATENT DOCUMENTS

| | | | |
|---|---|---|---|
| 7,820,615 B2* | 10/2010 | Malton | A61K 8/34 424/401 |
| 7,919,452 B2 | 4/2011 | Malton et al. | |
| 8,147,808 B2 | 4/2012 | Scavone et al. | |
| 8,632,755 B2 | 1/2014 | Scavone et al. | |
| 2003/0049290 A1 | 3/2003 | Jha et al. | |
| 2003/0194416 A1 | 10/2003 | Shefer et al. | |
| 2004/0091435 A1 | 5/2004 | Shefer et al. | |
| 2004/0109833 A1 | 6/2004 | Tang et al. | |
| 2004/0175404 A1 | 9/2004 | Shefer et al. | |
| 2004/0202632 A1 | 10/2004 | Gott et al. | |
| 2005/0003975 A1 | 1/2005 | Browne et al. | |
| 2006/0159639 A1 | 7/2006 | Ogura et al. | |
| 2006/0243322 A1* | 11/2006 | Heltovics | A61K 8/27 137/8 |
| 2006/0263311 A1 | 11/2006 | Scavone et al. | |
| 2006/0263312 A1 | 11/2006 | Scavone et al. | |
| 2006/0263313 A1 | 11/2006 | Scavone et al. | |
| 2006/0292098 A1 | 12/2006 | Scavone et al. | |
| 2007/0172382 A1* | 7/2007 | Uchiyama | A61L 9/14 422/5 |
| 2008/0213191 A1 | 9/2008 | Scavone et al. | |
| 2008/0213203 A1 | 9/2008 | Scavone et al. | |
| 2008/0213204 A1 | 9/2008 | Scavone et al. | |
| 2008/0215023 A1 | 9/2008 | Scavone et al. | |
| 2011/0212147 A1 | 9/2011 | Scavone et al. | |
| 2011/0212148 A1 | 9/2011 | Scavone et al. | |

FOREIGN PATENT DOCUMENTS

| | | |
|---|---|---|
| EP | 1 176 945 B1 | 11/2004 |
| EP | 1 280 509 B1 | 1/2005 |
| EP | 1 176 944 B1 | 9/2006 |
| EP | 1 331 920 B1 | 6/2007 |
| EP | 0 965 326 B1 | 7/2007 |
| EP | 1 289 484 B1 | 7/2007 |
| EP | 1 289 485 B1 | 9/2007 |
| EP | 1 330 234 B1 | 9/2007 |
| EP | 1 499 283 B1 | 7/2010 |
| EP | 1 331 921 B1 | 1/2011 |
| EP | 1 289 484 B2 | 4/2011 |
| WO | 98/56889 A1 | 12/1998 |
| WO | 00/67714 A1 | 11/2000 |
| WO | 00/67715 A1 | 11/2000 |
| WO | 2004/078154 A1 | 9/2004 |

OTHER PUBLICATIONS

International Search Report and Written Opinion of the International Searching Authority, PCT/US2014/025158, dated Aug. 1, 2014, 15 pages.

* cited by examiner

PERSONAL CARE COMPOSITIONS

TECHNICAL FIELD

The present disclosure generally relates to compositions including cyclic oligosaccharides, a fragrance, and a volatile solvent; and methods relating thereto.

BACKGROUND

Consumers often desire personal care compositions that deliver pleasant fragrances during and/or after application of the product. However, producing such products is often challenging for numerous reasons. For example, fragrances are often prematurely lost because many fragrances are relatively highly volatile and thus evaporate quickly after application. Because the amount of the fragrance that is released into the surrounding area generally decreases after application of a personal care composition, a consumer is likely to perceive potentially minimal or no fragrance odor character after time. Therefore, there is a need for improved personal care compositions that can deliver pleasant fragrances for extended periods of time during and after application of the product.

SUMMARY

An aerosolized composition comprising: a cyclic oligosaccharide; a fragrance; a volatile solvent; and a propellant; wherein the aerosolized composition is free of nonvolatile solvents.

A method for delivering an improved moisture-triggered fragrance release system comprising: contacting a suitable substrate with an aerosolized composition comprising a cyclic oligosaccharide; a fragrance; a volatile solvent; and a propellant; wherein the aerosolized composition is free of nonvolatile solvents.

DETAILED DESCRIPTION

While the specification concludes with the claims particularly pointing and distinctly claiming the invention, it is believed that the present invention will be better understood from the following description.

The devices, apparatuses, methods, components, and/or compositions of the present invention can include, consist essentially of, or consist of, the components of the present invention as well as other ingredients described herein.

All percentages and ratios used herein are by weight of the total composition and all measurements made are at 25° C., unless otherwise designated.

All measurements used herein are in metric units unless otherwise specified.

Reference within the specification to "embodiment(s)" or the like means that a particular material, feature, structure and/or characteristic described in connection with the embodiment is included in at least one embodiment, but it does not mean that all embodiments incorporate the material, feature, structure, and/or characteristic described. Furthermore, materials, features, structures and/or characteristics may be combined in any suitable manner across different embodiments and materials, features, structures and/or characteristics may be omitted or substituted from what is described.

"Free of" means that the stated ingredient has not been added to the composition. However, the stated ingredient may incidentally form as a byproduct or a reaction product of the other components of the personal care composition.

"Nonvolatile" refers to those materials that are liquid under ambient conditions and which have a measurable vapor pressure at 25° C. These materials typically have a vapor pressure less than about 0.01 mmHg, and an average boiling point typically greater than about 250° C.

"Soluble" means at least about 0.1 g of solute dissolves in 100 ml of solvent at 25' C and atm of pressure.

"Substantially free of" means an amount of a material comprises less than 1%, 0.5%, 0.25%, 0.1%, 0.05%, 0.01%, or 0.001% by weight of a composition.

Cyclic oligosaccharides, and in particular cyclodextrins, have been used as a means to deliver a moisture-triggered fragrance from non-polar systems. In this regard, a fragrance is typically encapsulated within the cyclodextrin and is released when moisture is introduced into the system. One of the challenges of delivering a similar moisture-triggered fragrance release system with a polar chassis is that the polar environment will typically release the fragrance within the system itself and not provide a long lasting fragrance.

Surprisingly, it has been found that limiting the amount of nonvolatile solvents in polar and aqueous compositions as described herein may dramatically improve the benefit of a long lasting fragrance provided by the cyclic oligosaccharides.

Cyclic Oligosaccharides

The compositions described herein may include a cyclic oligosaccharide. As used herein, the term "cyclic oligosaccharide" means a cyclic structure comprising six or more saccharide units. The cyclic oligosaccharides may have six, seven, or eight saccharide units or mixtures thereof. It is common in the art to refer to six, seven and eight membered cyclic oligosaccharides as α, β, and γ, respectively. Non-limiting examples of useful cyclic oligosaccharides include those that are soluble in water, ethanol, or both water and ethanol. The cyclic oligosaccharides useful herein may have a solubility of at least about 0.1 g/100 ml, at 25° C. and 1 atm of pressure in either water, ethanol, or both water and ethanol. The compositions disclosed herein may comprise from about 0.001% to about 40%, from about 0.1% to about 25%, from about 0.3% to about 20%, from about 0.5% to about 10%, or from about 0.75% to about 5%, by weight of the composition, of a cyclic oligosaccharide. The compositions disclosed herein may comprise from 0.001% to 40%, from 0.1% to 25%, from 0.3% to 20%, from 0.5% to 10%, or from 0.75% to 5%, by weight of the composition, of a cyclic oligosaccharide.

The cyclic oligosaccharide may comprise any suitable saccharide or mixture of saccharides. Examples of suitable saccharides include, but are not limited to, glucose, fructose, mannose, galactose, maltose, and mixtures thereof. The cyclic oligosaccharide, or mixture of cyclic oligosaccharides, may be substituted by any suitable substituent or mixture of substituents. Herein the use of the term "mixture of substituents" means that two or more different suitable substituents may be substituted onto one cyclic oligosaccharide. Suitable examples of substituents include, but are not limited to, alkyl groups, hydroxyalkyl groups, dihydroxyalkyl groups, carboxyalkyl groups, aryl groups, maltosyl groups, allyl groups, benzyl groups, alkanoyl groups, and mixtures thereof. These substituents may be saturated or unsaturated, straight or branched chain. For example, the substituents may include saturated and straight chain alkyl groups, hydroxyalkyl groups, and mixtures thereof. The alkyl and hydroxyalkyl substituents, for example, may also be selected from $C_1$-$C_8$ alkyl or hydroxyalkyl groups, alkyl and hydroxyalkyl substituents from $C_1$-$C_6$ alkyl or hydroxyalkyl groups, and alkyl and hydroxyalkyl substituents from $C_1$-$C_4$ alkyl or hydroxyalkyl groups. The alkyl and hydroxyalkyl substituents may be, for example, propyl, ethyl, methyl, and hydroxypropyl.

In addition to the substituents themselves, the cyclic oligosaccharides may have an average degree of substitution of at least 1.6, wherein the term "degree of substitution" means the average number of substituents per saccharide unit. For example, the cyclic oligosaccharides may have an average degree of substitution of less than about 2.8 or from about 1.7 to about 2.0. The average number of substituents may be determined using common Nuclear Magnetic Resonance techniques known in the art. Examples of cyclic oligosaccharides useful herein include methyl-α-cyclodextrins, methyl-β-cyclodextrins, hydroxypropyl-α-cyclodextrins, hydroxypropyl-β-cyclodextrins, and mixtures thereof.

The cyclic oligosaccharides may comprise a fragrance (e.g. a cyclodextrin-fragrance complex). Cyclodextrin particles and cyclodextrin complexes comprising a fragrance material may be formed by various methods. For example, a solvent (e.g., water), unloaded cyclodextrin particles, and a fragrance material can be placed into a container and then mixed for a period of time to permit loading of fragrance molecules into "cavities" of cyclodextrin molecules. The mixture may or may not be processed further; e.g., processed through a colloid mill and/or homogenizer. The solvent is then substantially removed from the resulting mixture or slurry to yield cyclodextrin-fragrance complex particles. Spray drying a slurry or mixture of cyclodextrin-fragrance complexes is another manufacturing technique capable of producing the cyclodextrin particles and cyclodextrin complexes.

Volatile Solvents

The compositions described herein may include a volatile solvent or a mixture of volatile solvents. The volatile solvents may comprise greater than or equal to 10%, greater than 30%, greater than 40%, greater than 50%, greater than 60%, or greater than 90%, and less than 99% by weight of the composition. The volatile solvents useful herein may be relatively odorless and safe for use on human skin. Suitable volatile solvents may include $C_1$-$C_4$ alcohols and mixtures thereof. For example, ethanol may be used as the volatile solvent. Some other non-limiting examples of volatile solvents include methanol, propanol, isopropanol, butanol, and mixtures thereof.

Nonvolatile Solvents

The composition may comprise a nonvolatile solvent or a mixture of nonvolatile solvents. Non-limiting examples of nonvolatile solvents include benzyl benzoate, diethyl phthalate, isopropyl myristate, propylene glycol, dipropylene glycol, triethyl citrate, and mixtures thereof. If present, the nonvolatile solvent may be included at a weight ratio of the nonvolatile solvent to the cyclic oligosaccharide of less than 1:1, less than 1:2, less than 1:10, or less than 1:100. The nonvolatile solvent may also be included at a weight ratio of the nonvolatile solvent to the cyclic oligosaccharide of less than about 1:1, less than about 1:2, less than about 1:10, or less than about 1:100, but greater than 0. The composition may also be free of nonvolatile solvents.

Fragrances

The composition may include a fragrance. As used herein, "fragrance" is used to indicate any odoriferous material. Any fragrance that is cosmetically acceptable may be used in the composition. For example, the fragrance may be one that is a liquid at room temperature. Generally, the fragrance(s) may be present at a level from about 0.01% to about 40%, from about 0.1% to about 25%, from about 0.25% to about 20%, or from about 0.5% to about 15%, by weight of the composition.

A wide variety of chemicals are known as fragrances, including aldehydes, ketones, and esters. More commonly, naturally occurring plant and animal oils and exudates comprising complex mixtures of various chemical components are known for use as fragrances. Non-limiting examples of the fragrances useful herein include pro-fragrances such as acetal pro-fragrances, ketal pro-fragrances, ester pro-fragrances, hydrolyzable inorganic-organic pro-fragrances, and mixtures thereof. The fragrances may be released from the pro-fragrances in a number of ways. For example, the fragrance may be released as a result of simple hydrolysis, by a shift in an equilibrium reaction, by a pH-change, or by enzymatic release. The fragrances herein may be relatively simple in their chemical make-up, comprising a single chemical, or may comprise highly sophisticated complex mixtures of natural and synthetic chemical components, all chosen to provide any desired odor.

The fragrances may have a boiling point (BP) of about 500° C. or lower, about 400° C. or lower, or about 350° C. or lower. The BP of many fragrances are disclosed in *Perfume and Flavor Chemicals* (Aroma Chemicals), Steffen Arctander (1969). The C log P value of the fragrances may be about 0.1 or greater, about 0.5 or greater, about 1.0 or greater, or about 1.2 or greater. As used herein, "C log P" means the logarithm to the base 10 of the octanol/water partition coefficient. The C log P can be readily calculated from a program called "C LOG P" which is available from Daylight Chemical Information Systems Inc., Irvine Calif., USA. Octanol/water partition coefficients are described in more detail in U.S. Pat. No. 5,578,563.

Suitable fragrances are also disclosed in U.S. Pat. No. 4,145,184, U.S. Pat. No. 4,209,417, U.S. Pat. No. 4,515,705, and U.S. Pat. No. 4,152,272. Non-limiting examples of fragrances include animal fragrances such as musk oil, civet, castoreum, ambergris, plant fragrances such as nutmeg extract, cardomon extract, ginger extract, cinnamon extract, patchouli oil, geranium oil, orange oil, mandarin oil, orange flower extract, cedarwood, vetyver, lavandin, ylang extract, tuberose extract, sandalwood oil, bergamot oil, rosemary oil, spearmint oil, peppermint oil, lemon oil, lavender oil, citronella oil, chamomille oil, clove oil, sage oil, neroli oil, labdanum oil, eucalyptus oil, verbena oil, mimosa extract, narcissus extract, carrot seed extract, jasmine extract, olibanum extract, rose extract, and mixtures thereof.

Other examples of suitable fragrances include, but are not limited to, chemical substances such as acetophenone, adoxal, aldehyde C-12, aldehyde C-14, aldehyde C-18, allyl caprylate, ambroxan, amyl acetate, dimethylindane derivatives, α-amylcinnamic aldehyde, anethole, anisaldehyde, benzaldehyde, benzyl acetate, benzyl alcohol and ester derivatives, benzyl propionate, benzyl salicylate, borneol, butyl acetate, camphor, carbitol, cinnamaldehyde, cinnamyl acetate, cinnamyl alcohol, cis-3-hexanol and ester derivatives, cis-3-hexenyl methyl carbonate, citral, citronnellol and ester derivatives, cumin aldehyde, cyclamen aldehyde, cyclo galbanate, damascones, decalactone, decanol, estragole, dihydromyrcenol, dimethyl benzyl carbinol, 6,8-dimethyl-2-nonanol, dimethyl benzyl carbinyl butyrate, ethyl acetate, ethyl isobutyrate, ethyl butyrate, ethyl propionate, ethyl caprylate, ethyl cinnamate, ethyl hexanoate, ethyl valerate, ethyl vanillin, eugenol, exaltolide, fenchone, fruity esters such as ethyl 2-methyl butyrate, galaxolide, geraniol and ester derivatives, helional, 2-heptonone, hexenol, α-hexylcinnamic aldehyde, hydroxycitrolnellal, indole, isoamyl acetate, isoeugenol acetate, ionones, isoeugenol, isoamyl iso-valerate, iso E super, limonene, linalool, lilial, linalyl acetate, lyral, majantol, mayol, melonal, menthol, p-methylacetophenone, methyl anthranilate, methyl cedrylone, methyl dihydrojasmonate, methyl eugenol, methyl ionone, methyl-α-naphthyl ketone, methylphenylcarbinyl acetate, mugetanol, γ-nonalactone, octanal, phenyl ethyl acetate, phenyl-acetaldehyde dimethyl acetate, phenoxyethyl isobutyrate, phenyl ethyl alcohol, pinenes, sandalore, santalol, stemone, thymol, terpenes, triplal, triethyl citrate, 3,3,5-trimethylcyclohexanol, γ-undecalactone, undecenal, vanillin, veloutone, verdox, and mixtures thereof.

Water

The compositions described herein may include water. If present, the water may comprise from about 0.1% to about 40%, from about 1% to about 30%, or from about 5% to about 20%, by weight, of the composition.

Propellant

The compositions described herein may include a propellant. Non-limiting examples of propellants include compressed air, nitrogen, inert gases, carbon dioxide, and mixtures thereof. Propellants may also include gaseous hydrocarbons like propane, n-butane, isobutene, cyclopropane, halogenated hydrocarbons like 1,1-difluoroethane, and mixtures thereof. Some non-limiting examples of propellants include 1,1,1,2,2-pentafluoroethane, 1,1,1,2-tetrafluoroethane, 1,1,1,2,3,3,3-heptafluoropropane, trans-1,3,3,3-tetrafluoroprop-1-ene, dimethyl ether, dichlorodifluoromethane (propellant 12), 1,1-dichloro-1,1,2, 2-tetrafluoroethane (propellant 114), 1-chloro-1,1-difluoro-2,2-trifluoroethane (propellant 115), 1-chloro-1,1-difluoroethylene (propellant 142B), 1,1-difluoroethane (propellant 152A), monochlorodifluoromethane, and mixtures thereof. Some other propellants suitable for use include, but are not limited to, A-46 (a mixture of isobutane, butane and propane), A-31 (isobutane), A-17 (n-butane), A-108 (propane), AP70 (a mixture of propane, isobutane and n-butane), AP40 (a mixture of propane, isobutene and n-butane), AP30 (a mixture of propane, isobutane and n-butane), and 152A (1,1 difluoroethane). The propellant may have a concentration from about 15%, 25%, 30%, 32%, 34%, 35%, 36%, 38%, 40%, or 42% to about 70%, 65%, 60%, 54%, 52%, 50%, 48%, 46%, 44%, or 42% by weight of the total fill of materials stored within the container.

Other Ingredients

The compositions disclosed herein may also contain a variety of other ingredients that may render the composition more cosmetically or aesthetically acceptable or provide the composition with additional usage benefits. These other ingredients are well-known to those skilled in the art. These include any cosmetically acceptable ingredient such as may be found in the CTFA *International Cosmetic Ingredient Dictionary and Handbook,* 7th edition, edited by Wenninger and McEwen, (*The Cosmetic, Toiletry, and Fragrance Association*, Inc., Washington, D.C., 1997). As used herein "cosmetically acceptable" means a material (e.g., compound or composition) that is suitable for use in contact with skin, hair, or other suitable substrate. For example, the compositions may include alcohol denaturants such as denatonium benzoate; UV stabilizers such as benzophenone-2; antioxidants such as tocopheryl acetate; preservatives such as phenoxyethanol, benzyl alcohol, methyl paraben, propyl paraben; dyes; pH adjusting agents such as lactic acid, citric acid, sodium citrate, succinic acid, phosphoric acid, sodium hydroxide, sodium carbonate; deodorants and antimicrobials such as farnesol and zinc phenolsulphonate; humectants such as glycerine; skin conditioning agents such as allantoin; cooling agents such as trimethyl isopropyl butanamide and menthol; hair conditioning ingredients such as panthenol, panthetine, pantotheine, panthenyl ethyl ether, and combinations thereof; silicones; salts in general, such as potassium acetate and sodium chloride; and mixtures thereof. When present, these additional ingredients may be present at a level of less than 10%, by weight, of the total composition.

Antiperspirant Active

The compositions described herein may be free of, substantially free of, or may include an antiperspirant active (i.e. any substance, mixture, or other material having antiperspirant activity). Examples of antiperspirant actives include astringent metallic salts, like the inorganic and organic salts of aluminum, zirconium and zinc, as well as mixtures thereof. Such antiperspirant actives include, for example, the aluminum and zirconium salts, such as aluminum halides, aluminum hydroxyhalides, zirconyl oxyhalides, zirconyl hydroxyhalides, and mixtures thereof.

Article of Manufacture

The composition may be included in a container comprising a spray dispenser. The container may further comprise a vessel for containing the composition to be dispensed. The container may comprise an aerosolized composition (i.e. a composition comprising a propellant) within the vessel as well. Other non-limiting spray dispensers include non-aerosol dispensers (e.g. vapor sprays), manually activated dispensers, pump-spray dispensers, or any other suitable dispenser available in the art.

Method of Use

The compositions described herein may be packaged with any container known in the art and with any spray dispenser suitable for delivering the composition to a substrate. The composition may be applied to any substance where moisture is available to trigger the release of the fragrance. When the composition is applied to the human body, the composition may be applied to any area of the skin or may be applied to any area of the body. Alternatively, the composition may be applied to any article, such as a fabric, or any absorbent article including, but not limited to, feminine hygiene articles, diapers, and adult incontinence articles. For example, the composition may be used as a body spray, feminine spray, adult incontinence spray, baby spray, or other spray.

Headspace Test Method

Prepare a 3 inch by 5 inch cardboard, professional aerosol testing blotter card (available from Orlandi Inc.) for each sample to be tested. Pre-weigh each blotter card with an analytical balance. Spray each sample evenly onto a blotter card. This can be done using a 3 ounce plastic bottle (Matrix Packaging) fitted with a 3 ounce spray actuator from Seaquist Perfect Dispensing. The blotter card should be weighed after the sample is sprayed to ensure that approximately 0.050 grams±0.0025 of sample was sprayed onto the blotter card. If the blotter card was not evenly wet among the application area upon visual evaluation or if the amount of sample sprayed was not approximately 0.050 grams±0.0025, the blotter card should be disposed and the process should be repeated.

Once all samples are prepared, the blotter card should be placed with the application side face up on a paper towel. The blotter card should be allowed to dry at room temperature for about 4 hours. After drying, using a similar plastic bottle fitted with the spray actuator as described above, spray each sample once with distilled water directly over the application area of the blotter card. Immediately after spraying, place each blotter card containing a sample into a different 7 ounce clear polyethylene terephthalate cup containing a lid. This can be done by rolling the blotter card into a cylinder across the long axis of the blotter card and arranging the blotter card so that the application side is facing the center of the cup. Once placed, the lid to the polyethylene terephthalate cup should be closed and the samples are then ready for analysis.

Next, prepare a zNose Fast-GC Analyzer (Model #MEA007100) with DB-624 column from Electronic Sensor Technology, Inc., (hereinafter referred to as "zNose") or equivalent for analysis. Prior to running the samples, the zNose should be cleaned and calibrated. To clean and calibrate the zNose, first turn on the zNose, open the helium valve, and open the program, MicroSense 4.5. Allow all parts of the instrument to reach their appropriate temperatures which can take approximately 15 minutes.

If the helium in the zNose is low, connect a helium tank to the back of the zNose (marked "Helium") by way of a hose, open the valve on the helium tank, and fill until the zNose pressure gauge reaches about 1000 psi. Once full, close the valve on the helium tank, release the pressure from the hose, and remove the hose from the zNose.

To clean the inlet and needle of the zNose, fill half of a vial with methanol and insert the bubbler so that the tip of the bubbler is fully emerged in the methanol. Place the vial on a sampler needle. In the control panel, type in 90 seconds and select "Pump" to bubble the methanol. Next, hit the "Fire Trap" twice in the control panel. Raise the column temperature to 190° C. in the test settings for 15 seconds. Once complete, reduce the column temperature back to 40° C. Back the sensor once by clicking the proper button on the monitoring tools. Run a high temperature blank, raising the sensor temperature to 100° C. and save this file. The blank should be an empty headspace of the same container in which the sampling is done. Run a low temperature blank by lowering the sensor temperature to 40° C. If large peaks remain, repeat the cleaning procedures as stated above. If large peaks remain after cleaning, refer to the Maintenance and Repair section in the zNose's accompanying manual. If peaks are less than 300 counts and are in higher KI, the contamination peaks may be tagged and accounted for in the calculations.

The zNose is clean and operational when all peaks are below 100 counts as per manufacturer's instructions. Ensure the 'Test settings' are set according to the following: Sensor (50C), Column (40C), Valve (145C), Inlet (200C), Trap (200C), Pump Time (10 seconds). Once test settings are set, calibrate the zNose with a n-alkanes standard as stated in the zNose's accompanying manual. This will ensure the zNose is operating according to the manufacturer's standards.

Once the zNose is clean and calibrated, create a new alarm file. The new alarm file should contain no tagged peaks. Samples should be analyzed randomly. Analyze the $1^{st}$ sample according to the manufacturer's instructions. A cleaning step should be performed after each sample is analyzed by bubbling methanol for 5 seconds. Next, a blank should be analyzed to ensure that no peaks remain. If no peaks remain, analyze the $1^{st}$ sample a second time. Perform a cleaning step with bubbling methanol for 5 seconds followed by an analysis of a blank to ensure that no peaks remain. If no peaks remain, analyze the $1^{st}$ sample a third time. Perform a cleaning step with bubbling methanol for 5 seconds followed by an analysis of a blank to ensure that no peaks remain. Repeat the above steps for each sample. All testing should take place within an hour from the analysis of the first sample and within 4 to 5 hours after the application of the sample to the blotter card.

Once all samples have been analyzed, transfer the data to Microsoft® Excel® or equivalent and sum the total area under all the peaks associated with each sample. For each sample, there should be a 'total peak area' representing each of the 3 runs per sample. Calculate the average, standard deviation, and the percent relative standard deviation (i.e., % RSD) for each sample. A mean, standard deviation, and % RSD should now be available for each sample based on a sample size of n=3.

Fragrance Expert Panel

Evaluations were conducted under controlled environmental conditions by a trained panel using the following standardized procedures. Approximately 10-20 expert panelists participated in each evaluation. Compositions were sprayed using a 3 ounce plastic bottle (Matrix Packaging) fitted with a 3 ounce spray actuator from Seaquist Perfect Dispensing. Compositions were shaken and then sprayed for 2 seconds onto the forearm of a panelist, approximately 2 to 6 inches below the wrist in an area preferably with minimal hair. The actuator was held about 6 inches away from the forearm. The process was repeated with the other forearm. Each panelist rated the intensity of the fragrance, from 1-8, in order of increasing intensity (e.g. a rating of 1 being the lowest intensity and a rating of 8 being the highest intensity) before application of the composition (baseline), and at 15 min, 30 min, and 60 min after spraying of the composition. At times 45 min, 90 min, and 180 min after spraying of the composition, the forearms were sprayed with one spritz of water using a 3 ounce plastic bottle (Matrix Packaging) fitted with a 3 ounce spray actuator from Seaquist Perfect Dispensing and the panelist rated the intensity before and after the water spritz. The ratings were recorded and subsequently analyzed by the Wilcoxon method.

Fragrance Untrained Panel

Evaluations were conducted under controlled environmental conditions by an untrained panel using the following standardized procedures. Approximately 5 untrained panelists participated in each evaluation. Compositions were sprayed onto a 3 inch by 5 inch cardboard, professional aerosol testing blotter card (available from Orlandi Inc.) using a 3 ounce plastic bottle (Matrix Packaging) fitted with a 3 ounce spray actuator from Seaquist Perfect Dispensing. An amount of 0.050 g±0.0025 of composition was applied to each blotter card. The amount sprayed onto each blotter card can be confirmed using an analytical balance. Following the spraying of the composition, the blotter cards were allowed to dry for 24 hours. After drying, blotter cards were sprayed with approximately 0.025 g of water using a 3 ounce plastic bottle (Matrix Packaging) fitted with a 3 ounce spray actuator from Seaquist Perfect Dispensing and placed into a 7 ounce clear polyethylene terephthalate cup for evaluation. Panelists were instructed to rate the intensity of the fragrances from 1-7 in order of increasing intensity (e.g. a rating of 1 being the lowest intensity and a rating of 7 being the highest intensity). The ratings were recorded and subsequently analyzed by the Wilcoxon method.

EXAMPLES

The following examples are given solely for the purpose of illustration and are not to be construed as limiting the invention, as many variations thereof are possible.

Table 1 below illustrates the effect of nonvolatile solvents on the release of a fragrance into the headspace from a cyclodextrin-fragrance complex. The total area count for the compositions shown in Table 1 was measured using the Headspace Test Method disclosed herein. Examples contained 0.25% by weight of the composition of a typical fragrance, 1% by weight of the composition of methylated-β-cyclodextrin (shown as "mβCD" in Table 1), and the nonvolatile solvents, dipropylene glycol or triethyl citrate, at the indicated percentiles. The remainder of the formulation was balanced to 100% with ethanol. Formulations were mixed to ensure homogeneity.

pylene glycol. These data suggest that the inclusion of nonvolatile solvents can suppress the release of a fragrance from a composition including methylated-β-cyclodextrin. The data further suggest that the ratio of nonvolatile solvent to methylated-β-cyclodextrin is an important consideration for formulating such compositions in view of maximizing the release of the fragrance into the headspace.

TABLE 1

|  | Example A | Example B | Example C | Example D | Example E | Example F | Example G | Example H | Example I |
|---|---|---|---|---|---|---|---|---|---|
| Ethanol | 98.75 | 98.74 | 98.74 | 98.65 | 98.65 | 98.26 | 98.26 | 97.76 | 97.76 |
| mβCD | 1.00 | 1.00 | 1.00 | 1.00 | 1.00 | 1.00 | 1.00 | 0.99 | 0.99 |
| Typical Fragrance | 0.25 | 0.25 | 0.25 | 0.25 | 0.25 | 0.25 | 0.25 | 0.25 | 0.25 |
| Dipropylene Glycol | 0 | 0.01 | — | 0.1 | — | 0.5 | — | 1.0 | — |
| Triethyl Citrate | 0 | — | 0.01 | — | 0.1 | — | 0.5 | — | 1.0 |
| Ratio of nonvolatile solvent to mβCD | NA | 1:100 | 1:100 | 1:10 | 1:10 | 1:2 | 1:2 | 1:1 | 1:1 |
| zNose Headspace Total Peaks * | 202268 | 159514 | 136332 | 70821 | 108203 | 52142 | 7008 | 10787 | 5256 |

* Znose Headspace Total Peaks excludes those contributed by the non-volatile solvents, dipropylene glycol and triethyl citrate.

Comparing Example B and Example C to Example A from Table 1, the addition of either dipropylene glycol or triethyl citrate decreased the amount of fragrance released into the headspace by approximately 21% and 33%, respectively. Increasing the concentration of either dipropylene glycol or triethyl citrate relative to methylated-β-cyclodextrin in the composition further decreased the amount of fragrance released into the headspace in a dose-dependent manner. For example, comparing Example D to Example B, increasing the concentration of dipropylene glycol relative to methylated-β-cyclodextrin decreased the amount of fragrance released into the headspace from a count of 159514 for Example B to a count of 70821 for Example D. Comparing Example H to Example A from Table 1, the inclusion of dipropylene glycol in the composition at a ratio of 1:1 of dipropylene glycamethylated-β-cyclodextrin reduced the amount of fragrance released into the headspace by approximately 95%. Similar trends were observed when triethyl citrate was included in the composition in place of dipropylene glycol.

Table 2 below illustrates the influence of nonvolatile solvents on the release of a fragrance into the headspace as determined by the Fragrance Untrained Panel described herein. Example 1 included a ratio of nonvolatile solvent to methylated-β-cyclodextrin due to trace amounts of dipropylene glycol within the fragrance itself. Example 1, which contained the least amount of nonvolatile solvent relative to methylated-β-cyclodextrin, obtained the highest average ranking by the Fragrance Untrained Panel with a score of 7.0. Comparing Example 2 to Example 1, increasing the concentration of the nonvolatile solvent, dipropylene glycol, relative to methylated-β-cyclodextrin to a ratio of 1:4 resulted in average ranking of 6.0, a ranking statistically significantly lower than that attributed to Example 1. Comparing Example 3 to Example 1, increasing the concentration of the nonvolatile solvent, triethyl citrate, relative to methylated-β-cyclodextrin to a ratio of 1:5 resulted in an average ranking of 3.8, a statistically significantly lower ranking than attributed to Example 1.

TABLE 2

| Material | Example 1 | Example 2 | Example 3 | Example 4 | Example 5 | Example 6 | Example 7 |
|---|---|---|---|---|---|---|---|
| Denatured Alcohol | 93 | 92.07 | 92.07 | 88.35 | 88.35 | 83.7 | 83.7 |
| Dipropylene Glycol | 0 | 1 | 0 | 5 | 0 | 10 | 0 |
| Triethyl Citrate | 0 | 0 | 1 | 0 | 5 | 0 | 10 |
| Cavasol W7 mβCD | 5 | 4.95 | 4.95 | 4.75 | 4.75 | 4.5 | 4.5 |
| Fragrance | 2 | 1.98 | 1.98 | 1.9 | 1.9 | 1.8 | 1.8 |
| Ratio Nonvolatile solvent: mβCD | 1:25 | 1:4 | 1:5 | 1:1 | 1:1 | 2:1 | 2:1 |
| Average Panelist Ranking | 7.0 | 6.0 | 3.8 | 3.6 | 2.8 | 2.6 | 2.2 |

Comparing Example 4 and Example 6 to Example 2, further increasing the concentration of the nonvolatile solvent, dipropylene glycol, relative to methylated-β-cyclodextrin to a ratio of 1:1 (Example 4) or 2:1 (Example 6) resulted in an average ranking of 3.6 and 2.6, respectively; a ranking statistically significantly lower than that attributed to Example 2. No significant difference was observed between Example 4 and Example 3, Example 5 and Example 3, Example 6 and Example 3, or Example 7 and Example 3. These data corroborate the findings obtained from the Headspace Test Method that the inclusion of nonvolatile solvents in such compositions can suppress the release of a fragrance and that the ratio of nonvolatile solvent to methylated-β-cyclodextrin is an important consideration for formulating such compositions in view of maximizing the release of the fragrance into the headspace.

Table 3 below illustrates the effect of nonvolatile solvents on the release of a fragrance into the headspace in aerosolized compositions as determined by the Fragrance Expert Panel described herein. Table 3 illustrates the average ratings of Panelists who rated the forearms of subjects 180 min after the spraying of Example 8, 9, and 10, before and after a spritz of water. Example 8 included the nonvolatile solvents, dipropylene glycol and isopyopryl myristate, but did not include methylated-β-cyclodextrin. Example 9 included methylated-β-cyclodextrin and the nonvolatile solvents, dipropylene glycol and isopyopryl myristate. Example 10 included methylated-β-cyclodextrin but did not include the nonvolatile solvents, dipropylene glycol and isopyopryl myristate.

TABLE 3

| Material | Example 8 | Example 9 | Example 10 |
|---|---|---|---|
| Denatured Alcohol | 34.35 | 33.35 | 46.00 |
| Dipropylene Glycol | 12.41 | 11.41 | 0 |
| Isopropyl Myristate | 0.83 | 0.83 | 0 |
| Zinc Phenosulphonate | 0.41 | 0.41 | 0 |
| Cavasol W7 mβCD | 0 | 2.00 | 2.00 |
| Fragrance | 1.32 | 1.32 | 1.32 |
| Propane | 6.163 | 6.163 | 6.163 |
| Isobutane | 34.381 | 34.381 | 34.381 |
| 1,1-Difluoroethane (HFC-152a) | 10.136 | 10.136 | 10.136 |
| Ratio Nonvolatile solvent: mβCD | NA | 5:1 | NA |
| Average Panelist Ranking (3 hour pre-mist) | 4.3 | 4.6 | 4.6 |
| Average Panelist Ranking (3 hour post-mist) | 4 | 4.5 | 4.9 |

Comparing Example 8 to Example 9, the addition of methylated-β-cyclodextrin to the composition of Example 9 did not result in a statistically significant increase in the average ranking despite the increase in average scores when ratings were conducted before the application of the water. In contrast, after the application of water, Example 9 had a statistically significant increase in rating as compared to Example 8 (4.5 versus 4). Comparing Example 9 to 10, the exclusion of nonvolatile solvents as in Example 10 did not result in a statistically significant increase in the ranking by the Panelists as compared to Example 9 when ratings were conducted before the application of the water. Surprisingly, the exclusion of nonvolatile solvents as in Example 10 resulted in a statistically significant increase in the average ranking as compared to Example 9 when ratings were conducted after the application of water (4.9 versus 4.5).

These data corroborate the findings obtained from the Headspace Test Method and the Fragrance Untrained Panel that the inclusion of nonvolatile solvents in such compositions can suppress the release of a fragrance.

Table 4 below illustrates another example of an aerosolized composition. Example 11 includes 1,1-Difluoroethane, methylated-β-cyclodextrin, denatured alcohol, water, and a fragrance.

TABLE 4

| Material | Example 11 |
|---|---|
| Denatured Alcohol | 61.25 |
| Water | 0.75 |
| Dipropylene Glycol | 0 |
| Cavasol W7 mβCD | 1.00 |
| Fragrance | 2.00 |
| 1,1-Difluoroethane (HFC-152a) | 35.00% |

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any related patent or application identified in the Application Data Sheet accompanying this application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. An aerosol composition comprising:
   i) methyl-β-cyclodextrin;
   ii) from about 30% to about 60%, by weight of the composition, of a volatile solvent;
   iii) from about 25% to about 60%, by weight of the composition of a propellant;

iv) a fragrance; and v) optionally, a nonvolatile solvent;

wherein the weight ratio of the nonvolatile solvent, when present, to the methyl-β-cyclodextrin is less than 1:25.

2. The aerosol composition of claim 1, further comprising an antimicrobial.

3. The aerosol composition of claim 1, wherein at least a portion of the methyl-β-cyclodextrin is complexed with the fragrance.

4. The aerosol composition of claim 1, wherein the weight ratio of the nonvolatile solvent, when present, to the methyl-β-cyclodextrin is less than 1:100.

5. The aerosol composition of claim 1, wherein the methyl-β-cyclodextrin is spray dried.

6. The aerosol composition of claim 1, wherein the volatile solvent comprises alcohol.

7. The aerosol composition of claim 1, wherein the composition is free of the nonvolatile solvent.

\* \* \* \* \*